United States Patent [19]

DeLuca et al.

[11] Patent Number: 5,030,772

[45] Date of Patent: Jul. 9, 1991

[54] PROCESS FOR PREPARING VITAMIN $D_2$ COMPOUNDS AND THE CORRESPONDING 1 α-HYDROXYLATED DERIVATIVES

[76] Inventors: Hector F. DeLuca, Deerfield; Heinrich K. Schnoes, Madison, both of Wis.; Shigeya Okada, Hirakatashi, Japan

[21] Appl. No.: 481,990

[22] Filed: Feb. 14, 1990

[51] Int. Cl.$^5$ .................. C07C 35/22; C07C 35/37
[52] U.S. Cl. .................. 568/817; 568/822; 568/823; 568/838
[58] Field of Search ............... 568/715, 822, 823, 835, 568/838, 817,

[56] References Cited

U.S. PATENT DOCUMENTS

| | | | |
|---|---|---|---|
| 3,585,221 | 6/1971 | DeLuca | 514/167 |
| 3,880,894 | 4/1975 | DeLuca et al. | 260/397.2 |
| 4,226,787 | 10/1980 | DeLuca et al. | 260/397.2 |
| 4,260,549 | 4/1981 | DeLuca et al. | 260/397.2 |
| 4,448,721 | 5/1984 | DeLuca et al. | 514/167 |
| 4,554,106 | 11/1985 | DeLuca et al. | 514/167 |
| 4,847,012 | 7/1989 | DeLuca et al. | 568/817 |

FOREIGN PATENT DOCUMENTS

| | | | |
|---|---|---|---|
| 108046 | 9/1976 | Japan | 568/838 |
| 108048 | 9/1976 | Japan | 568/838 |
| 108049 | 9/1976 | Japan | 568/838 |

*Primary Examiner*—Werren B. Lone
*Attorney, Agent, or Firm*—Andrus, Sceales, Starke & Sawall

[57] ABSTRACT

This invention relates to hydroxylated derivatives of vitamin $D_2$ and a process for preparing such compounds. In particular, a process for preparing the 24-epimer of vitamin $D_2$ and the corresponding 1α-hydroxylated derivative thereof is disclosed. The vitamin $D_2$ derivatives would find application in the treatment of or prophylaxsis for various disease states characterized by calcium and phosphorous imbalances.

13 Claims, No Drawings

PROCESS FOR PREPARING VITAMIN $D_2$ COMPOUNDS AND THE CORRESPONDING 1 α-HYDROXYLATED DERIVATIVES

TECHNICAL FIELD

This invention relates to biologically active vitamin D compounds.

More specifically, this invention relates to a process for the preparation of hydroxylated derivatives of vitamin $D_2$.

BACKGROUND OF THE INVENTION

The D vitamins are very important agents for the control of calcium and phosphate metabolism in animals and humans, and have long been used as dietary supplements and in clinical practice to assure proper bone growth and development. It is now know that the in vivo activity of these vitamins, specifically of vitamin $D_2$ and $D_3$, is dependent on metabolism to hydroxylated forms. Thus, vitamin $D_3$ undergoes two successive hydroxylation reactions in vivo, leading first to 25-hydroxyvitamin $D_3$ and then to 1,25-dihydroxyvitamin $D_3$ and the latter is thought to be the compound responsible for the well-known beneficial effects of vitamin $D_3$. Likewise, vitamin $D_2$, which is commonly used as a dietary supplement, undergoes an analogous hydroxylation sequence to its active forms, being first converted to 25-hydroxyvitamin $D_2$ (25-OH-$D_2$) and then to 1,25-dihydroxyvitamin $D_2$ (1,25-(OH)$_2D_2$). These facts are well established and well known in the art [see, for example, Suda et al. Biochemistry 8, 3515 (1969) and Jones et al. Biochemistry 14, 1250 (1975)].

Like the metabolites of the vitamin $D_3$ series, the hydroxylated forms of vitamin $D_2$ named above are, because of their potency and other beneficial properties, highly desirable dietary supplements, or pharmaceutical agents, for the cure or prevention of bone or related diseases, and their value and possible use is recognized in patents relating to these compounds [U.S. Pat. Nos. 3,585,221 and 3,880,894].

Whereas many metabolites of vitamin $D_3$ have been prepared by chemical synthesis, there has been less work on the preparation of vitamin $D_2$ metabolites. The known synthetic processes for the metabolites of the $D_3$-series (especially as far as they relate to the preparation of side chain hydroxylated compounds) are, of course, in general not suitable for the preparation of the corresponding vitamin $D_2$ metabolites, since the latter are characterized by a side chain structure (i.e. presence of a double bond and an extra methyl group) which requires a different synthetic approach from that applicable to side chain hydroxylated $D_3$ compounds.

Various approaches for the preparation of vitamin $D_2$ metabolites are known, and are described in U.S. Pat. Nos. 4,448,721, 4,847,012 and 4,769,181. Other preparations of 25-OH-$D_2$ and 1,25-(OH)$_2D_2$ compounds involving condensation of side chains with a steroid nucleus are shown in Yamada et al, "Facile And Stereoselective Synthesis of 25-Hydroxyvitamin $D_2$", Tetrahedron Letters, Vol. 25, No. 33, pp. 3347–3350, 1984 and in Tsuji et al, "A New And Convenient Synthesis of 1α, 25-Dihydroxyvitamin $D_2$ And Its 24R-Epimer," Bull. Chem. Soc. Jpn., Vol. 62, No. 10, pp. 3132–3137, 1989. Perlman et al have reported the preparation of the epimer of 1α-OH-$D_2$ by condensation of a suitable side chain fragment with a vitamin D nucleus in J. Chem. Soc. Chem. Com. pp. 1113–1115, 1989.

DISCLOSURE OF INVENTION

A novel and convenient synthesis of vitamin $D_2$ compounds has now been developed and is described herein. This synthesis provides vitamin $D_2$ and the 24-epimer of vitamin $D_2$, namely 24epi-vitamin $D_2$ (24-epi $D_2$), characterized by the structures shown below (where $X_1$ is hydrogen and $R_1$, $R_2$ and $R_3$ are methyl),

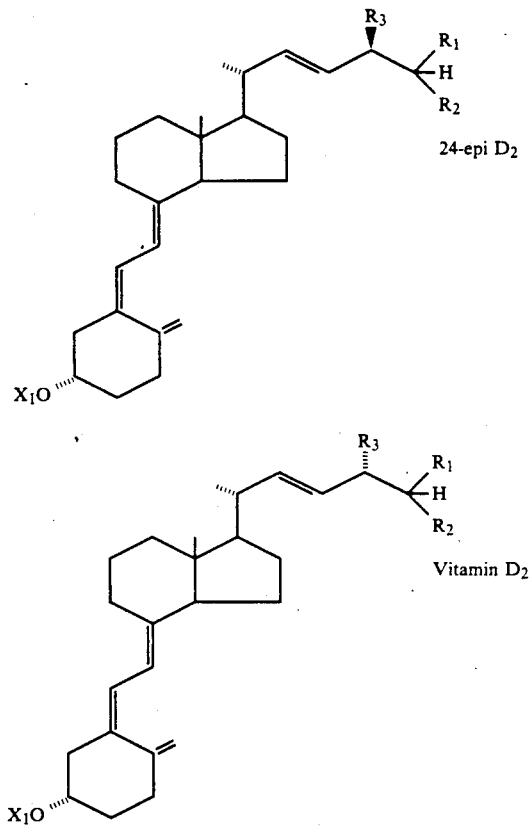

as well as the corresponding alkyl or aryl analogs, characterized by the structures above where $R_1$ and $R_2$ are alkyl (other than methyl) or aryl, and the corresponding side chain substituted derivatives where $R_3$ is alkyl, hydroxy, protected hydroxy (as defined below for $X_1$), hydrogen or fluorine, and the hydroxy-protected derivatives of these compounds characterized by the structures above, where $X_1$ is selected from the group consisting of acyl, alkylsilyl, or alkoxyalkyl.

In addition, the present process provides the 5,6-trans-isomers of the above compounds. Furthermore, the above compounds can be 1α-hydroxylated by known methods, so as to produce the corresponding 1α-hydroxyvitamin D derivatives. Especially preferred examples of the latter are 1α-hydroxy vitamin $D_2$ and 1α-24-epi-vitamin $D_2$.

The term "acyl", as used in this specification or in the claims, signifies an aliphatic acyl group of from 1 to about 6 carbons, in all possible isomeric forms (e.g. formyl, acetyl, propionyl, butyryl, isobutyryl, valeryl, etc.), or an aromatic acyl group (aroyl group) such as benzoyl, the isomeric methyl-benzoyls, the isomeric nitro- or halobenzoyls, etc., or a dicarboxylic acyl group of from 2 to 6 atoms chain length, i.e. acyl groups of the type ROOC(CH$_2$)$_n$CO—, or ROCC- H₂—O—CH₂CO—, where n has values between 0 and 4 inclusive and R is hydrogen or an alkyl radical, such as oxalyl, malonyl, succinoyl, glutaryl, adipyl, diglycolyl. The term "alkyl" refers to a lower alkyl group of 1 to 6 carbons in all possible isomeric forms, e.g. methyl, ethyl, propyl, isopropyl, butyl, isobutyl, sec.-butyl, pentyl, etc., and the word "aryl" signifies a phenyl or substituted phenyl group, e.g. alkylphenyl, methoxyphenyl, etc. The term "alkylsilyl" refers to trialkyl silicone groupings where the alkyl groups may be the same or different as exemplified by trimethylsilyl, triethylsilyl, dimethyl-tert.-butylsilyl and similar groupings. The term "alkoxyalkyl" refers to protecting groups such as methoxymethyl, ethoxymethyl, methoxyethoxymethyl, and similar alkoxymethyl groups, as well as the related cyclic structures, such as tetrahydropyranyl or tetrahydrofuranyl.

The overall process developed for the preparation of the above compounds may be divided into two general phases, namely (a) addition of a completed, preformed side chain fragment to a suitable steroidal precursor to produce a 5,7-diene steroid as the central intermediate, and (b) conversion of this 5,7-diene to the vitamin D structure to produce the desired vitamin D compound, and, if desired, (c) further conversion of the latter product to the corresponding 1α-hydroxyvitamin D compound. This process avoids the relatively difficult step of isomer separation which is required after conversion in the process of U.S. Pat. No. 4,448,721. The process of the present invention also increases the yield of the end product since it utilizes a completed, performed pure isomer side chain fragment to make the desired end product, rather than a mixture of side chain isomers as in U.S. Pat. No. 4,448,721.

In general terms, the process of this invention comprises the reaction of a steroidal 22-aldehyde of the structure:

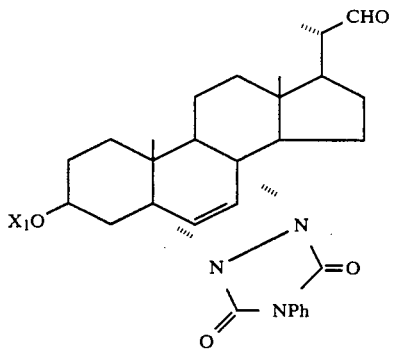

where $X_1$ is hydrogen or a hydroxy-protecting group, with a sulfone derivative of the general formula, ArSO₂CH₂R where Ar represents a phenyl or tolyl group, and R is selected from the group consisting of straight or branched, substituted or unsubstituted, hydrocarbon radicals of from 1 to 25 carbon atoms, where the substituents are selected from the group consisting of hydroxy, protected hydroxy, and fluorine.

The coupling reaction, conducted in a basic medium, between the above aldehyde and sulfone derivatives, yields a condensation product of the formula:

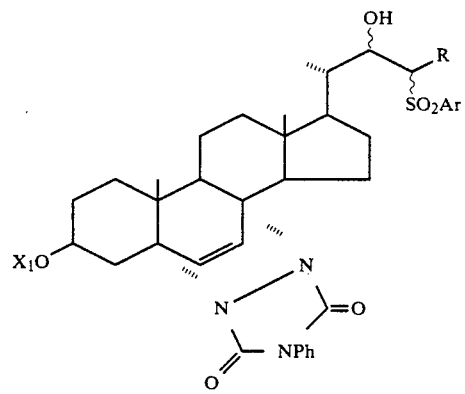

which is then subjected to reduction (either as the 22-hydroxy, or as the corresponding 22-O-acylated derivative) using metal amalgams (Na, Al, Zn amalgams) or related dissolving metal reduction systems, so as to provide the 22,23-unsaturated steroid of the formula:

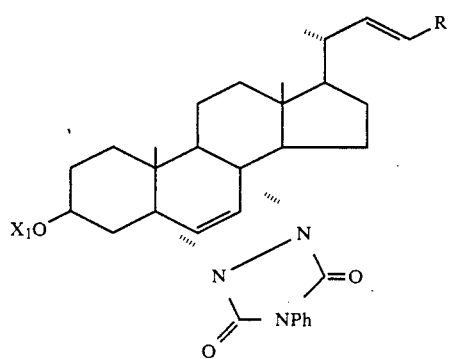

where R and $X_1$ represent the groupings defined above. This steroid intermediate can then be further converted by known reactions to the desired vitamin D compounds.

It is readily apparent that by suitable variation of R in the aryl sulfone derivative used in the above coupling process a range of different vitamin D compounds can be produced.

The reaction sequence illustrated by Process Scheme I presents a specific embodiment of the overall process, whereas Process Scheme II illustrates preparation of an appropriate side chain unit for addition to the steroid-22-aldehyde as shown in Scheme I.

Starting materials for the present process are steroidal 22-aldehydes, such as, for example, the PTAD-diene-protected-22-aldehyde (4) shown in Scheme I (where PTAD refers to the phenyltriazoline-3,5-dione-protecting group shown), which in turn can be prepared from ergosterol by the known steps (Scheme I).

The first step of this process comprises the addition of a suitable side chain fragment. Thus, condensation of aldehyde (4) with a sulfonyl-side chain fragment as shown in the Scheme I (sulfone (20), further described below) present in the form of its anion, in an ether or hydrocarbon solvent, provides the hydroxy-sulfone intermediate (5). The anion of the sulfone (20) side chain fragment is generated by treatment of the sulfone with a strong base, such as lithium diethylamide, n-butyl lithium or methyl or ethyl magnesium bromide (or similar Grignard reagent) in an ether or hydrocarbon solvent, and to this solution of sulfone anion the steroid aldehyde (compound 4) as an ether or hydrocarbon solution is then added. The reaction is best effected under an inert atmosphere.

The next step comprises the removal of the hydroxy- and phenylsulfonyl groups in the side chain with formation of the 22(23)-trans-double bond. Thus, treatment of compound (5), in methanol solution saturated with $NaHPO_4$, with sodium amalgam under an inert atmosphere, gives compound (6) featuring the desired trans-22-double bond in the side chain. If desired, the 22-hydroxy group in compound (5) can also be acylated or sulfonylated (e.g. mesylated) prior to the Na/Hg-reduction step, but this is not generally required.

It is to be noted that, as shown in Process Scheme I, addition of the side chain fragment, sulfone (20), to the aldehyde (4), does not cause epimerization at the asymetric center of carbon 20, i.e. the stereo-chemistry at that center is retained, as is required. If desired, retention of stereochemistry at carbon 20 may be checked at this stage of the synthesis by the conversion of intermediates of type (6) back to the original aldehyde starting materials. For example, subjecting compound (6) to ozonolysis with reductive work-up, using fully conventional and standard conditions, yields the corresponding C-22-aldehyde, i.e. the aldehyde of structure (4). Spectroscopic and chromatographic comparison of the aldehyde obtained from ozonolysis with the original starting material confirms retention of C-20 stereochemistry.

The next operation of the process involves conversion of these ring B-protected steroids to the desired 5,7-diene intermediate (7). In the case of the PTAD-diene-protected compound (6), this conversion is accomplished in a single step, namely treatment of (6) with a strong hydride reducing agent (e.g. $LiAlH_4$) in an ether solvent at reflux temperature gives the diene (7).

Conversion of 5,7-diene (7) to the final vitamin D products (9) or (14) comprises a sequence of several steps. The sequence shown in Process Scheme I involves first the irradiation of an ether or hydrocarbon solution of the 5,7-diene (7) with ultraviolet light to yield the previtamin analog (8) which by warming (50°-90° C.) in a suitable solvent (e.g. ethanol, hexane) undergoes isomerization to the vitamin $D_2$ compound (9).

Thereafter, compound (9) may be converted to the $1\alpha$-hydroxyvitamin $D_2$ compound (14) by the known steps shown in Scheme I. Reference is made to U.S. Pat. Nos. 4,260,549 and 4,554,106 for the prior art relevant to these transformations.

The side chain fragment, sulfone (20), as used in Scheme I is specifically the (S) enantiomer. Therefore, compounds (9) or (14) are obtained as the C-24-S-epimers, 24-epi-vitamin $D_2$ (9) or $1\alpha$-hydroxy-24-epi-vitamin $D_2$ (14), respectively. Thus, compounds (9) or (14) are prepared in epimerically pure form, and C-24-epimer separation as required in the process disclosed in U.S. Pat. No. 4,448,721, is not necessary. Use of the (R)-epimer of sulfone (20) in the present process yields specifically vitamin $D_2$, as well as, of course, the respective $1\alpha$-hydroxyvitamin $D_2$ compound.

The 5,7-diene (7) may be used as the free hydroxy compound or as its hydroxy-protected form, where the hydroxy-protecting groups (at C-3) may be acyl, alkyl-silyl or alkoxyalkyl groups as previously defined. Thus, the vitamin $D_2$ product will be obtained as the free hydroxy compound or, if desired, as the C-3-hydroxy-protected derivatives. Synthesis according to Scheme I would provide the vitamin $D_2$ products as the free hydroxy compounds but analogous conversion of 5,7-diene intermediate (7) as the 3-protected, derivative will yield the corresponding hydroxy-protected derivatives of the vitamin $D_2$ products.

The individual vitamin $D_2$ epimers, i.e. vitamin $D_2$ or 24-epi-$D_2$ (9) when obtained in the free hydroxy forms, are also conveniently hydroxy-protected at the C-3 position, by conventional reactions known in the art. Thus, vitamin $D_2$ may be acylated to yield, for example, the vitamin $D_2$-3-acetate. Other hydroxy-protecting groups can be introduced by analogous known reactions.

In addition to the hydroxy-protected derivatives, the 5,6-trans-isomers of 24-epi-$D_2$ as well as the $1\alpha$-hydroxy compounds are compounds of potential utility in medical applications because of their considerable vitamin D-like activity. These 5,6-transcompounds are prepared from the 5,6-cis-isomers (i.e. 9 or 14) by iodine catalyzed isomerization according to the procedures of Verloop et al. Rec. Trav. Chim. Pays Bas 78, 1004 (1969), and the corresponding 3-hydroxy-protected derivatives are likewise obtained by analogous isomerization of the corresponding 5,6-cisacylates, or by hydroxy-protection of the 5,6-trans-$D_2$ compounds.

The required side chain fragment, sulfone (20), can be prepared according to Perlman et al, supra, or according to the process shown in Process Scheme II. This synthesis is straightforward and involves as a first step dissolving alcohol (17) in anhydrous pyridine and reacting it with p-toluenesulfonyl chloride to provide the tosylate (18). Tosylate (18) is dissolved in a solution of anhydrous dimethyl formamide and reacted with thiophenol and t-BuOK to yield the sulfide (19). The sulfide (19) in turn is dissolved in dichloromethane and reacted with 3-chloroperoxybenzoic acid to give the sulfone compound (20). The corresponding (R)-epimer of sulfone (20) can also be prepared according to Perlman et al supra, or according to Process Scheme II, using as starting material the alcohol corresponding to (17) but having the (R) configuration at carbon-2.

Furthermore, the present process also serves as a convenient method for the synthesis of vitamin-$D_2$ analogs, of the formula (30) shown below, or of the corresponding $1\alpha$-hydroxy-analogs,

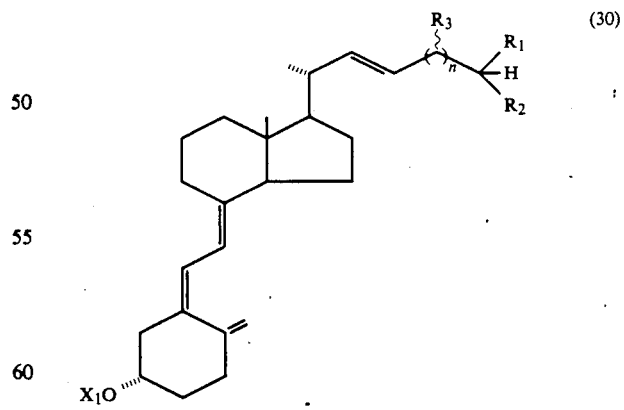

where n is an integer having a value of from 1 to 5, $X_1$ is selected from hydrogen and a hydroxy-protecting group, $R_3$ is alkyl, hydroxy, protected hydroxy, hydrogen or fluorine, and where $R_1$ and $R_2$, which may be the same or different, is an alkyl group other than methyl or an aryl group and where the C-24-group has either the (R)- or the (S)-stereochemical orientation. These compounds are prepared by condensing compound (4) with the appropriate alkyl or aryl side chain fragment as shown by the following formulae,

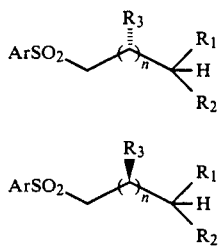

where $R_1$, $R_2$, $R_3$ and n are as defined above.

The use of compounds (31) and (32) as side chain units in the synthetic process depicted is in Scheme I, then provides the $D_2$- or 24-epi-$D_2$-homologs of general structure (30) or the corresponding 1α-hydroxylated derivatives, where $R_1$, $R_2$ and $R_3$ represent alkyl or aryl residues such as ethyl, propyl, isopropyl, butyl, isobutyl, pentyl, hexyl, phenyl, etc.

Since the compounds, where $R_1$, $R_2$, or $R_3$ represent higher homologs of methyl, are generally more lipophilic, the alkyl- or aryl-analogues represented by structure (30) above or their 5,6-trans-isomers, are expected to have utility in applications where a greater degree of lipophilicity is desired.

The present invention is further described by means of the following illustration. In this illustration, numerals designating specific products, e.g. compounds 1, 2, 3 etc. refer to the structures so numbered in Process Schemes I or II.

EXAMPLE 1

Ergosterol Method

To a solution of ergosterol 1 in anhydrous pyridine is added acetic anhydride. The mixture is stirred at room temperature overnight and water is added. The precipitate is filtered off, washed several times with water and recrystallized from ethanol to obtain 2.

To a solution of the precipitate 2 in chloroform is added 4-phenyl-1, 2, 4-triazoline-3,5-dione. The solution is stirred at room temperature and pyridine is added. The solution is cooled and treated with an ozone-oxygen mixture (TLC control) and thoroughly purged with nitrogen. Dimethyl sulfide is added and the mixture is washed with water, 2N HCl and then water again. The organic layer is separated and each washing is extracted with chloroform. The combined extract is dried over $Na_2SO_4$ and concentrated in vacuo. The residue is purified by silica gel chromatography to obtain compound 4.

To a stirred solution of sulfone 20, diisopropyl amine and anhydrous tetrahydrofuran (containing 1,10-phenanthroline as indicator) under nitrogen atmosphere is added n-BuLi (1.6M in hexane). The solution is stirred under nitrogen, then, compound 4 in anhydrous tetrahydrofuran is added. The mixture is stirred, decomposed by the addition of saturated $NH_4Cl$ solution, warmed and extracted three times with ethyl acetate. Each extract is washed with saturated NaCl solution, dried over $Na_2SO_4$ and concentrated in vacuo. The residue is purified on a silica gel column to afford compound 5.

A mixture of hydroxysulfones 5, 5% sodium amalgum and methanol saturated with $Na_2HPO_4$ is stirred under nitrogen atmosphere. The reaction solution is decanted and concentrated in vacuo. The residue is dissolved in ethyl acetate and washed with water. The ethyl acetate extract is separated and each washing is extracted twice with ethyl acetate. The combined extract is dried over $Na_2SO_4$ and concentrated in vacuo to obtain 6.

To a solution of compound 6 in tetrahydrofuran is added $LiAlH_4$. The mixture is heated under reflux and nitrogen atmosphere, cooled with ice water and decomposed by the dropwise addition of ethyl acetate and water. Then, the mixture is filtered and the filtrate is concentrated in vacuo. The residue is dissolved in ethyl acetate and washed twice with saturated NaCl solution. The ethyl acetate extract is separated and each washing is extracted with ethyl acetate. The combined extract is dried over $Na_2SO_4$ and concentrated in vacuo. Then, the residue is purified on a silica gel column to provide compound 7.

Compound 7 is dispersed in a mixture of ether and benzene (4:1) and irradiated with stirring under nitrogen in a water-cooled quartz immersion well equipped with an ozone free filter using a high-pressure UV lamp. The reaction may be monitored by HPLC.

The solution is concentrated in vacuo, redissolved in ethanol and heated under reflux and nitrogen. Then, the solution is concentrated in vacuo and the residue is purified on a silica gel column to obtain compound 9.

To a solution of compound 9 in anhydrous pyridine is added tosyl chloride. The mixture is stirred under nitrogen. Then, the solution is poured into a cold saturated $NaHCO_3$ solution. The mixture is allowed to stand for 30 min and extracted three times with a mixture of ether and dichloromethane (4:1). Each extract is washed with saturated NaCl solution, cold diluted HCl solution twice, saturated NaCl solution, saturated $NaHCO_3$ solution and saturated NaCl solution. The combined extract is dried over $Na_2SO_4$ and concentrated in vacuo. Compound 10 is obtained and converted to 11 without further purification.

Anhydrous $KHCO_3$ is dissolved in anhydrous methanol under nitrogen. To this solution is added dropwise a solution of compound 10 in anhydrous dichloromethane. The mixture is stirred under nitrogen. Then, the solution is concentrated in vacuo, the residue is dissolved in a mixture of ether and dichloromethane (4:1) and washed twice with water. The organic extract is separated and each washing is extracted twice with the same mixture of ether and dichloromethane. The combined extract is dried over $Na_2SO_4$ and concentrated in vacuo to obtain Compound 11 which is hydroxylated without further purification.

Tert-butyl hydroperoxdde (3.0M in 2,2-4-trimethyl-pentane) is added to a suspension of selenium dioxide in anhydrous dichloromethane. The mixture is stirred at room temperature under nitrogen. Anhydrous pyridine is added followed by a solution of compound 11 in anhydrous dichloromethane. The mixture is stirred under nitrogen at room temperature and heated under reflux. Then, a 10% NaOH solution is added and the mixture is extracted with ether. Each extract is washed with a 10% NaOH solution and a saturated NaCl solution. The combined extract is dried over $Na_2SO_4$ and concentrated in vacuo. The residue is purified on a silica gel column to obtain compound 12.

Compound 12 is dissolved in acetic acid and heated under nitrogen. Then, the solution is poured over ice and neutralized with saturated $NaHCO_3$ solution. The mixture is extracted three times with a mixture of ether and dichloromethane (4:1). Each extract is washed with a saturated NaHCO$_3$ solution and a saturated NaCl solution. The combined extract is dried over Na$_2$SO$_4$ and concentrated in vacuo. Then, to a solution of the residue in ethyl acetate is added maleic anhydride and the mixture is allowed to stand under nitrogen at room temperature. Then, the solution is concentrated in vacuo, the residue is redissolved in ether. KOH in methanol is added, the solution is stirred at room temperature and concentrated in vacuo. The residue is dissolved in a mixture of ether and dichloromethane (4:1) and washed with a 10% NaOH solution twice and a saturated NaCl solution. The organic extract is separated and each washing is extracted twice with the same mixture of ether and dichloromethane. The combined extract is dried over Na$_2$SO$_4$ and concentrated in vacuo. The residue is purified on a silica gel column using a mixture of ethyl acetate in hexane as eluant to obtain compound 14.

EXAMPLE 2

Intermediates for Side Chain

A mixture of compound 17, tosyl chloride and pyridine is stirred overnight. Then, the reaction mixture is dissolved in ether and washed with water, diluted HCl, water and saturated NaHCO$_3$ solution. The ether extract is separated and each washing is extracted twice with ether. The combined extract is dried over Na$_2$SO$_4$ and concentrated in vacuo. The residue is purified on a silica gel column to give tosylate (18).

To a stirred solution of thiophenol in anhydrous dimethyl formamide t-BuOK is added followed by compound 18 in anhydrous dimethyl formamide. The mixture is stirred overnight, dissolved in ice water and extracted with ethyl acetate. Each extract is washed with a saturated NaHCO$_3$ solution and water, combined, dried over Na$_2$SO$_4$ and concentrated in vacuo. Compound 19 is obtained and oxidized without further purification.

Compound 19 is dissolved in dichloromethane and cooled with ice water. To this solution is added m-chloroper benzoic acid slowly, the mixture is stirred at room temperature for 2 hrs and filtered. The filtrate is washed with a saturated NaHCO$_3$ solution twice, a saturated Na$_2$SO$_3$ solution for twice and a saturated NaHCO$_3$ solution. The organic phase is separated and each washing is extracted twice with dichloromethane. The combined extract is dried over Na$_2$SO$_4$, concentrated in vacuo and recrystallized from a mixture of ethyl acetate in hexane to form compound 20.

PROCESS SCHEME I

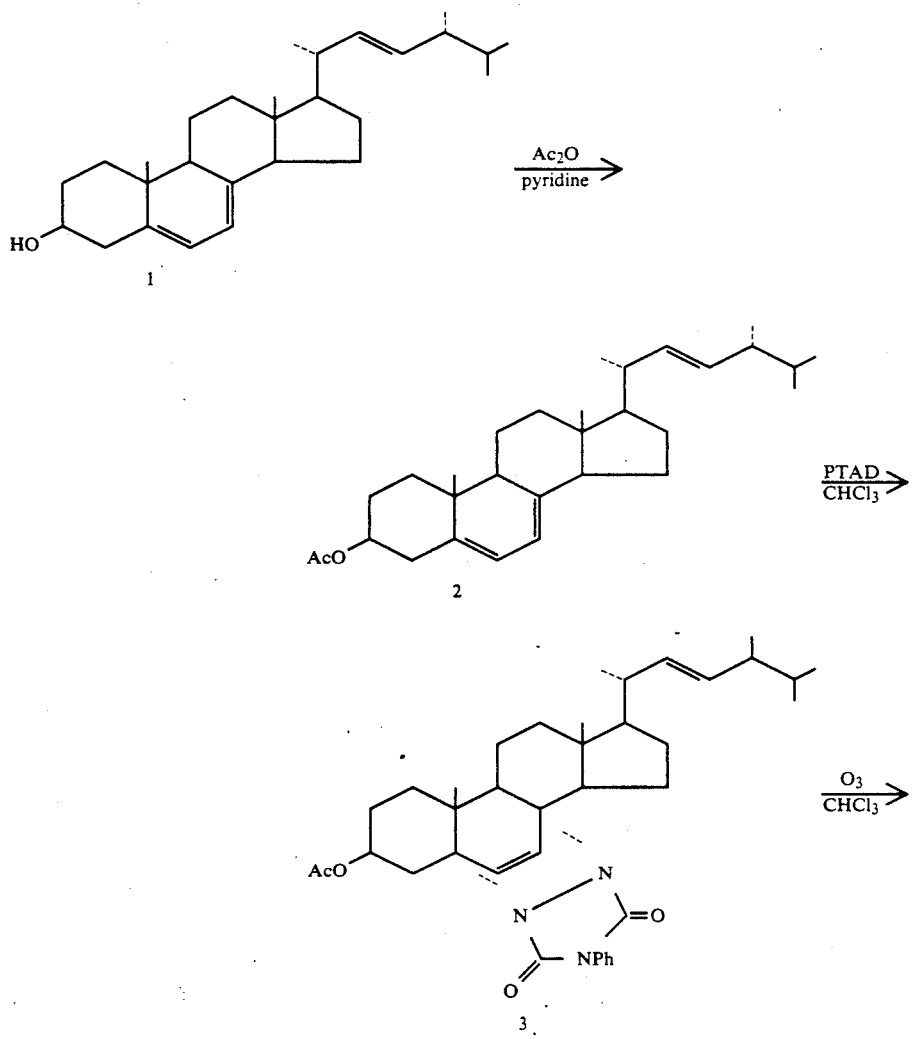

-continued
PROCESS SCHEME I
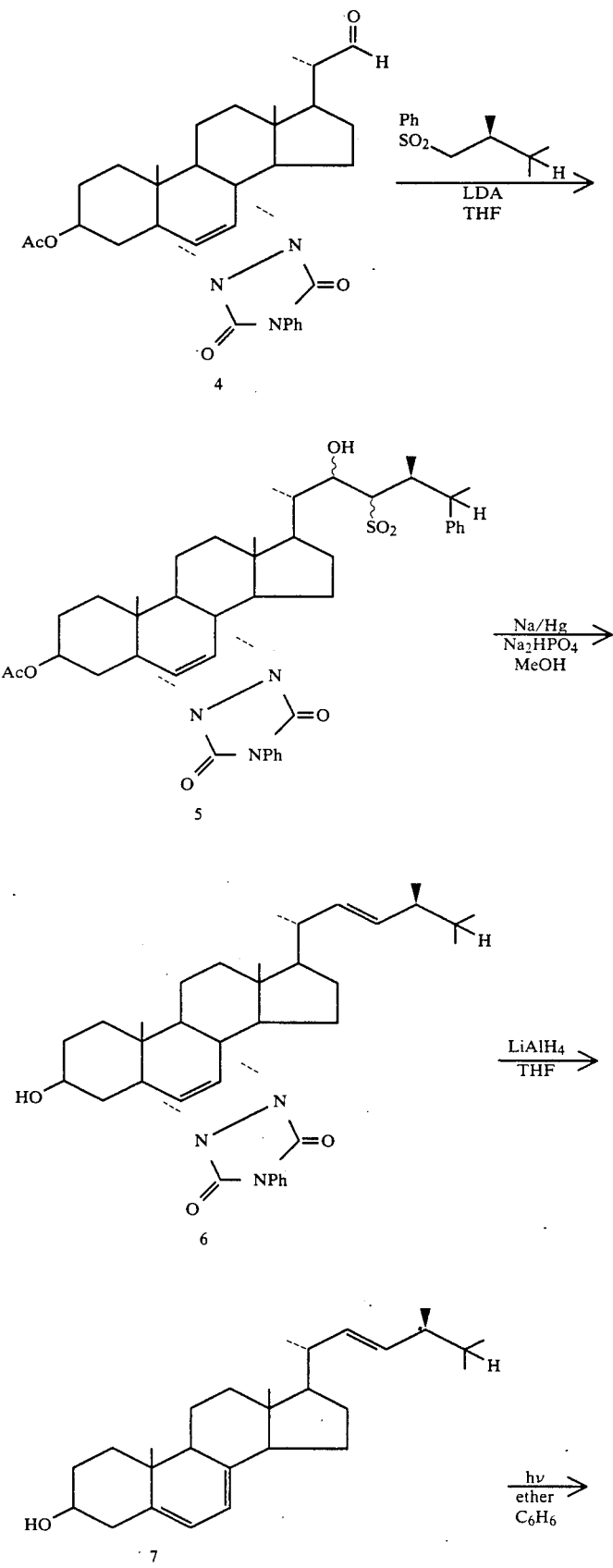

-continued
PROCESS SCHEME I
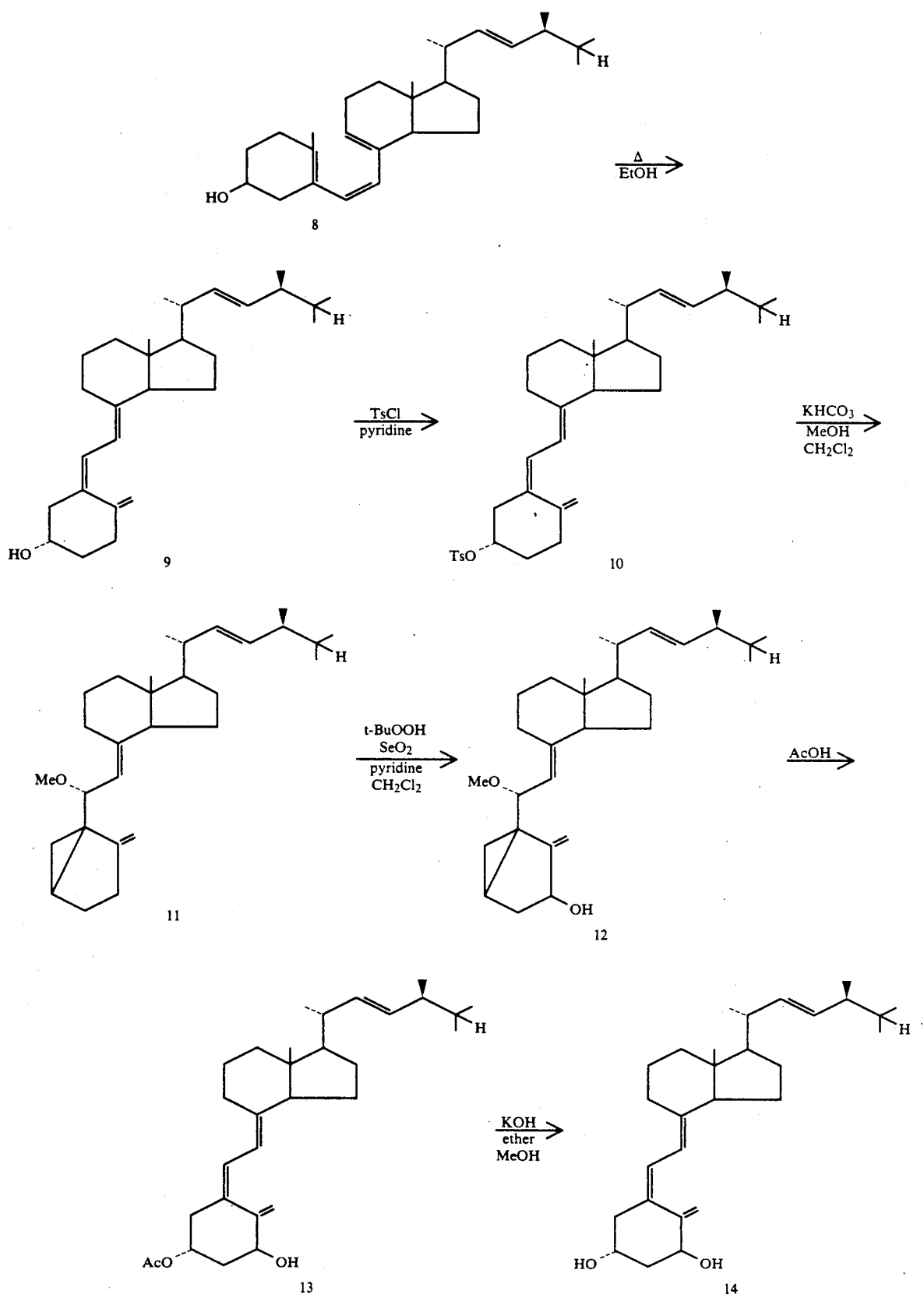

PROCESS SCHEME II

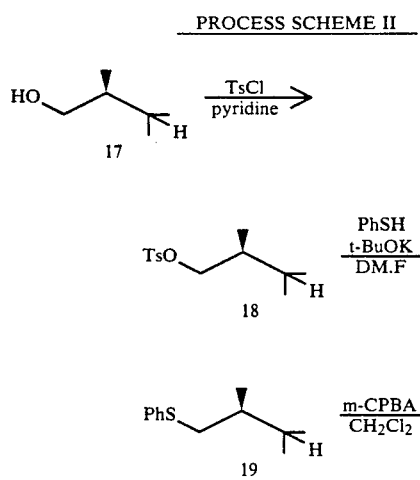

We claim:

1. A method for preparing vitamin D compounds having the formula

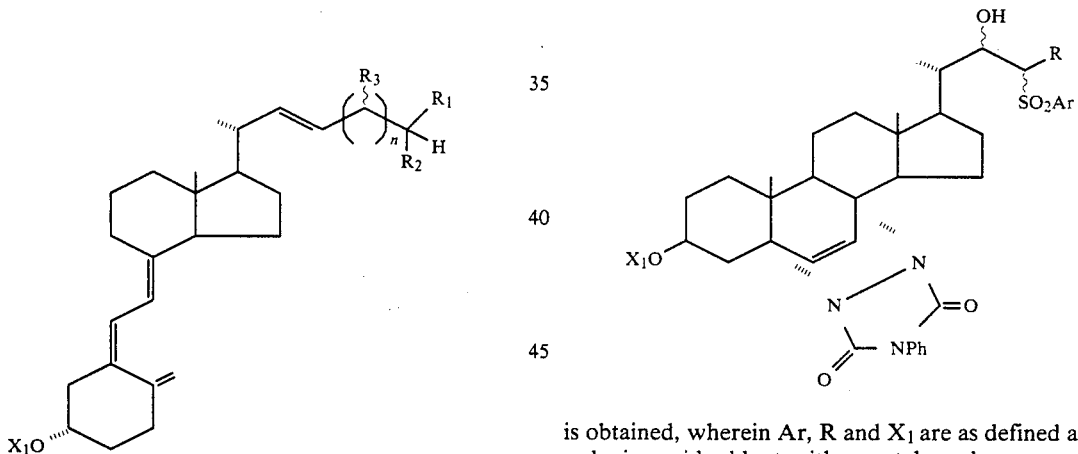

where $R_3$ can have either the R or S configuration and wherein n is an integer having a value of from 1 to 5, $X_1$ is selected from hydrogen or a hydroxy protecting group, $R_3$ is selected from an alkyl of 1 to 6 carbon atoms, hydroxy, protected hydroxy, hydrogen or fluorine, and where $R_1$ and $R_2$, which may be the same or different, are each selected from an alkyl of 1 to 6 carbon atoms or an aryl, said aryl selected from the group consisting of a phenyl or a substituted phenyl, which comprises condensing in the presence of a strong base in an organic solvent at a temperature below 0° C. a steroidal aldehyde of the formula

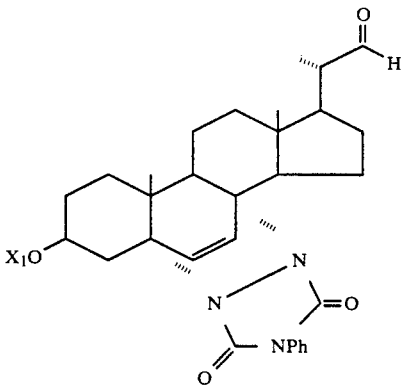

wherein $X_1$ is as defined above, with an arylsulfone of the formula $$ArSO_2CH_2R$$

wherein Ar is selected from the group consisting of a phenyl and a tolyl, and R is selected from the group consisting of an alkyl of from 1 to 25 carbon atoms, hydroxylated alkyl, hydroxy-protected hydroxylated alkyl, fluoro-substituted alkyl, fluoro-substituted hydroxylated 'alkyl and fluoro-substituted hydroxy-protected alkyl, whereby a hydroxy-sulfonyl adduct of the formula

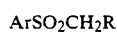

is obtained, wherein Ar, R and $X_1$ are as defined above, reducing said adduct with a metal amalgum reagent in an organic solvent at a temperature of from about 0° C. to about ambient to obtain an intermediate of the formula

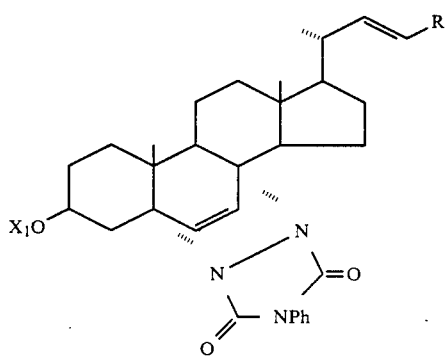

wherein R and $X_1$ are as defined above, and converting said intermediate to obtain the desired vitamin D compound.

2. The method of claim 1 wherein $X_1$ is hydrogen.
3. The method of claim 1 wherein $R_1$ and $R_2$ are both an alkyl group of 1 to 6 carbon atoms.
4. The method of claim 1 wherein R is a hydroxylated alkyl group or a hydroxy-protected hydroxylated alkyl group of from 1 to 25 carbon atoms.
5. The method of claim 1 wherein R is a fluoro-substituted alkyl group of from 1 to 25 carbon atoms.
6. The method of claim 1 wherein R is a fluoro-substituted hydroxylated alkyl group of from 1 to 25 carbon atoms, or a fluoro-substituted hydroxy-protected alkyl group of from 1 to 25 carbon atoms.
7. The method of claim 1 wherein the vitamin D compound is 24-epi-vitamin $D_2$.
8. The method of claim 1 wherein the vitamin D compound is vitamin $D_2$.
9. A method for preparing 24-epi-vitamin $D_2$ having the formula

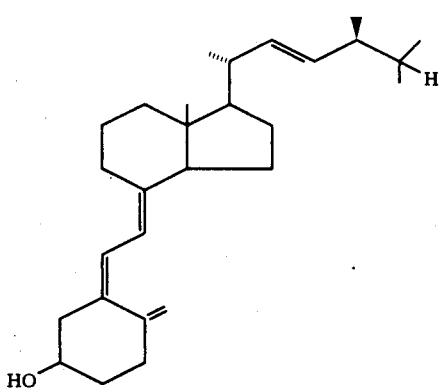

which comprises condensing in the presence of a strong base in an organic solvent at a temperature below 0° C. a steroidal aldehyde of the formula

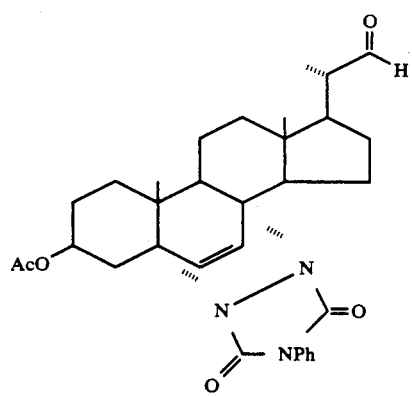

with a phenylsulfone of the formula

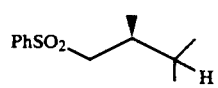

whereby a hydroxy-sulfonyl adduct of the formula

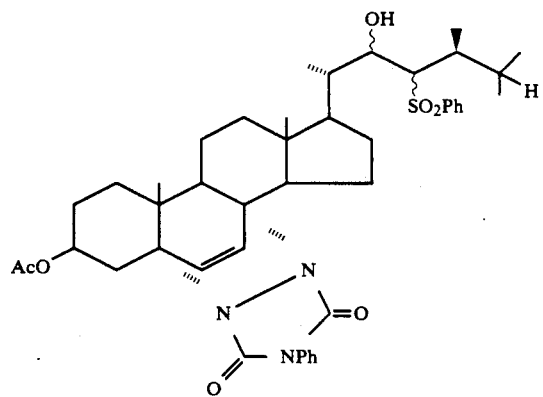

is obtained, reducing said adduct with a metal amalgum reagent in an organic solvent at a temperature of from about 0° C. to about ambient to obtain an intermediate of the formula

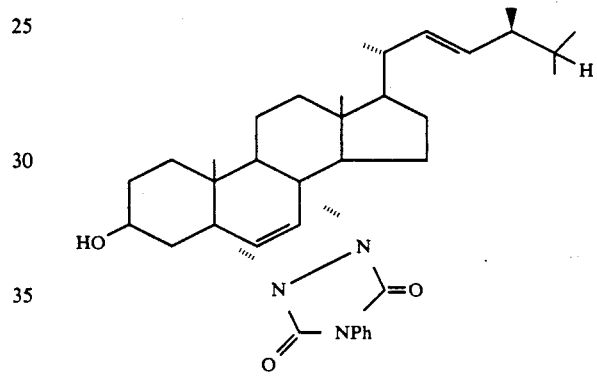

and converting said intermediate to obtain 24-epi-vitamin $D_2$.

10. The method of claim 9 wherein the 24-epi-vitamin $D_2$ compound is further subjected to a 1α hydroxylation process so as to obtain the corresponding 1α hydroxylated-24-epi-vitamin $D_2$ compound.

11. A method for preparing vitamin $D_2$ having the formula

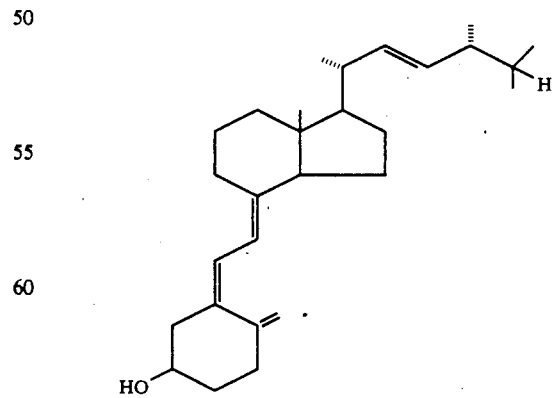

which comprises condensing in the presence of a strong base in an organic solvent at a temperature below 0° C. a steroidal aldehyde of the formula

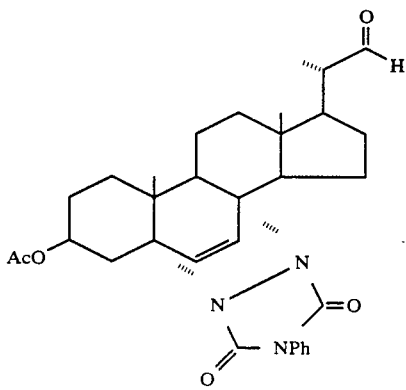

with a phenyl sulfone of the formula

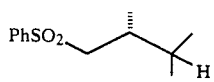

whereby a hydroxy-sulfonyl adduct of the formula

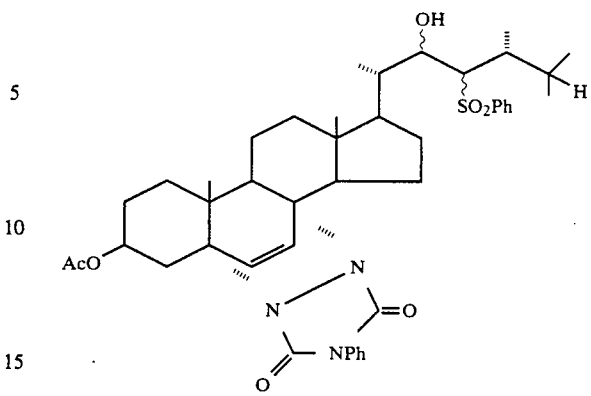

is obtained, reducing said adduct with a metal amalgum reagent in an organic solvent at a temperature of from about 0° C. to about ambient to obtain an intermediate of the formula

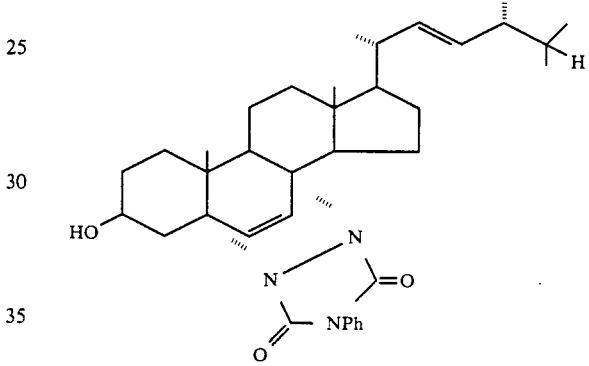

and converting said intermediate to obtain vitamin $D_2$.

12. The method of claim 11 wherein the vitamin $D_2$ compound is further subjected to a $1\alpha$ hydroxylation process so as to obtain the corresponding $1\alpha$ hydroxylated vitamin $D_2$ compound.

13. The method of claim 1 wherein the vitamin D compound is further subjected to a $1\alpha$ hydroxylation process so as to obtain the corresponding $1\alpha$ hydroxylated vitamin D compound.

* * * * *